US008770029B2

(12) United States Patent
Falter et al.

(10) Patent No.: US 8,770,029 B2
(45) Date of Patent: Jul. 8, 2014

(54) METHOD AND APPARATUS FOR ULTRASONIC TESTING

(75) Inventors: Stephan Falter, Simmerath (DE); Roman Koch, Blankenbach (DE)

(73) Assignee: General Electric Company, Schenectady, NY (US)

( * ) Notice: Subject to any disclaimer, the term of this patent is extended or adjusted under 35 U.S.C. 154(b) by 219 days.

(21) Appl. No.: 13/252,435

(22) Filed: Oct. 4, 2011

(65) Prior Publication Data
US 2013/0081468 A1   Apr. 4, 2013

(51) Int. Cl.
G01N 29/04 (2006.01)
G01N 29/06 (2006.01)

(52) U.S. Cl.
USPC .................. 73/618; 73/602; 73/610

(58) Field of Classification Search
USPC ........... 73/618–625, 609–610, 612, 614–615, 73/617, 598, 600, 606, 602
See application file for complete search history.

(56) References Cited

U.S. PATENT DOCUMENTS

| | | | | |
|---|---|---|---|---|
| 3,610,820 A * | 10/1971 | Lund | | 73/612 |
| 3,857,052 A * | 12/1974 | Beller | | 367/13 |
| 3,999,422 A * | 12/1976 | Lehmann et al. | | 73/614 |
| 4,106,346 A * | 8/1978 | Matzuk | | 73/614 |
| 4,312,229 A * | 1/1982 | Hurwitz et al. | | 73/603 |
| 4,372,323 A * | 2/1983 | Takemura et al. | | 600/447 |
| 4,437,348 A * | 3/1984 | Sasaki | | 73/625 |
| 4,457,178 A * | 7/1984 | Turbe et al. | | 73/636 |
| 4,471,449 A * | 9/1984 | Leavitt et al. | | 348/160 |
| 4,608,868 A * | 9/1986 | Green | | 73/606 |
| 4,653,328 A * | 3/1987 | Herman | | 73/602 |
| 4,730,495 A * | 3/1988 | Green | | 73/620 |
| 4,768,155 A * | 8/1988 | Takishita et al. | | 702/39 |
| 4,836,026 A * | 6/1989 | P'an et al. | | 73/620 |
| 4,862,892 A * | 9/1989 | Green | | 600/443 |
| 4,894,806 A * | 1/1990 | Jen et al. | | 367/7 |
| 4,947,351 A * | 8/1990 | Moran et al. | | 702/39 |
| 5,119,678 A * | 6/1992 | Bashyam et al. | | 73/602 |
| 5,203,335 A * | 4/1993 | Noujaim et al. | | 600/447 |
| 5,230,340 A * | 7/1993 | Rhyne | | 600/447 |
| 5,235,982 A * | 8/1993 | O'Donnell | | 600/443 |
| 5,313,947 A * | 5/1994 | Micco | | 600/455 |
| 5,381,693 A * | 1/1995 | Kobayashi et al. | | 73/614 |
| 5,481,917 A * | 1/1996 | Arima et al. | | 73/621 |
| 5,750,895 A * | 5/1998 | Chern et al. | | 73/614 |
| 6,443,896 B1* | 9/2002 | Detmer | | 600/445 |
| 7,617,730 B2* | 11/2009 | Georgeson | | 73/602 |
| 7,753,847 B2* | 7/2010 | Greenleaf et al. | | 600/438 |
| 7,779,694 B2* | 8/2010 | Iizuka | | 73/622 |
| 7,849,747 B2* | 12/2010 | Owens | | 73/598 |
| 7,917,317 B2* | 3/2011 | McKeon | | 702/66 |
| 8,286,467 B2* | 10/2012 | Fatemi et al. | | 73/105 |
| 2003/0167849 A1* | 9/2003 | Yamamoto et al. | | 73/620 |
| 2004/0118210 A1* | 6/2004 | Tooma et al. | | 73/625 |
| 2007/0266790 A1* | 11/2007 | Gunasekaran et al. | | 73/624 |
| 2010/0101326 A1* | 4/2010 | Iizuka et al. | | 73/588 |

* cited by examiner

*Primary Examiner* — Helen Kwok
(74) *Attorney, Agent, or Firm* — Global Patent Operation; Mark A. Conklin

(57) ABSTRACT

A method for ultrasonic testing of an object, the method comprising ultrasonic scanning of a plurality of scan regions of the object; converting ultrasonic echoes of the ultrasonic scanning into a plurality of electrical signals; gating the electrical signals to provide gated signals; and wherein different gating times are used for the electrical signals.

17 Claims, 7 Drawing Sheets

METHOD AND APPARATUS FOR ULTRASONIC TESTING

BACKGROUND OF THE INVENTION

The subject matter described herein relates to methods for ultrasonic testing of an object, to ultrasonic testing devices, and to methods for testing an object with an ultrasonic testing device.

Known ultrasonic testing devices for material testing include an ultrasonic transducer. The ultrasonic transducer is used to generate ultrasonic waves that are transmitted into the material. The transducer is also used for receiving echoes of ultrasonic waves propagating through the material. The echoes include reflections of flaws or other discontinuities in the material. The echo is converted into an electrical signal by a transducer. By presenting this signal in a so-called "A-mode image" or "A-scan", a user is able to identify flaws and discontinuities in the material.

At least some known ultrasonic testing devices are capable of generating and presenting a so-called "B-mode-image" or "B-scan". The B-mode image represents a two-dimensional echogram of the tested material. In B-mode images, the information of a plurality of A-mode images representing a plurality of scans of the material in several regions is displayed. A special type of a B-mode image is the so-called "sector scan" or "S-Scan", hereinafter referred to as the "S-mode image". A S-mode image with inclined scans of the material is usually generated in case a phased array transducer is used.

Time-controlled gating is used for cutting off regions of the material which are not of interest for the actual investigation. The gating start time or the gating finish time is set in one of the A-mode images. The gating times are then used for all electrical signals when generating the B-mode image individually. However, such a method encounters specific challenges when it comes to flaws with a general geometry, for instance, a geometry not aligned parallel to the surface of the material.

Accordingly, it is desirable to provide a method for ultrasonic scanning and an apparatus for ultrasonic scanning capable of handling flaws with general geometries.

BRIEF DESCRIPTION OF THE INVENTION

In one aspect, a method for ultrasonic testing of an object is provided. A method for ultrasonic testing of an object includes ultrasonic scanning of a plurality of scan regions of the object and converting ultrasonic echoes of the ultrasonic scanning into a plurality of electrical signals. After the conversion step, the electrical signals are gated to provide gated signals, wherein different gating times are used for the electrical signals.

In another aspect, an ultrasonic testing device for testing an object is provided. An ultrasonic testing device for testing an object includes an ultrasonic transducer for scanning a plurality of scan regions of the object and for converting ultrasonic echoes into electrical signals. Furthermore, a gating unit configured for gating the electrical signals with a gating time to provide gated signals is provided, wherein the gating time depends on the respective scan region.

In yet another aspect, a method for testing an object is provided with an ultrasonic testing device comprising a display, the method including scanning a plurality of scan regions of the object to obtain a plurality of electrical signals; and processing the electrical signals to obtain a B-mode image. An input from a user is received to set a boundary in the B-mode image; and, the electrical signals are processed, wherein the processing includes a gating of the electrical signals depending on the coordinates of the boundary in the B-mode image.

Further aspects, advantages, and features of the present invention are apparent from the dependent claims, the description, and the accompanying drawings.

BRIEF DESCRIPTION OF THE DRAWINGS

A full and enabling disclosure, including the best mode thereof, to one of ordinary skill in the art, is set forth more particularly in the remainder of the specification, including reference to the accompanying figures wherein.

DETAILED DESCRIPTION OF THE INVENTION

Reference will now be made in detail to the various embodiments, one or more examples of which are illustrated in the figures. Within the following description of the drawings, the same reference numbers refer to the same components. Generally, only the differences with respect to individual embodiments are described. Each example is provided by way of explanation and is not meant as a limitation. For example, features illustrated or described as part of one embodiment can be used on or in conjunction with other embodiments to yield yet further embodiments. It is intended that the present disclosure includes such modifications and variations.

The embodiments described herein include an ultrasonic testing device that may be used for testing materials. Typical embodiments provide an A-mode image or a B-mode image of a region of the tested object including the material.

As used herein, the term "objects" is intended to be representative of objects of materials, e.g., blocks of metal or ceramic, pipes, particularly steel pipes, or aluminum billets. Typical objects include any bodies made of steel, aluminum, copper alloys, and compounds including carbon compounds and ceramic compounds.

Figure 1:
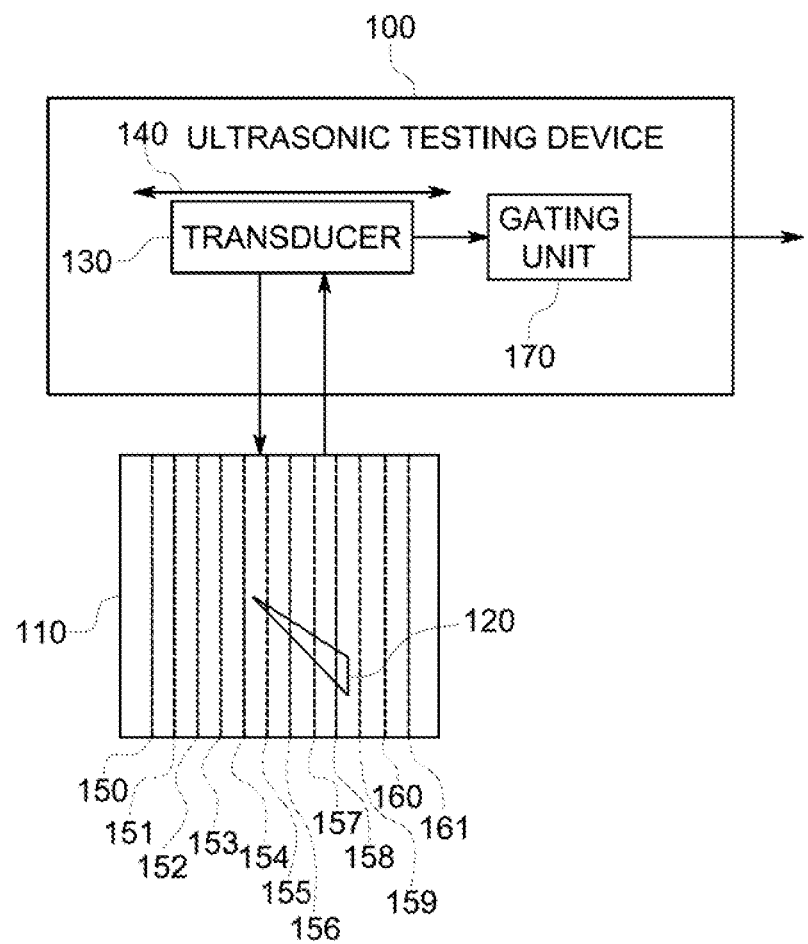
FIG. 1 is a schematic view of an ultrasonic scanning device according to embodiments.

FIG. 1 is a schematic view of an exemplary ultrasonic testing device 100 used for testing an object 110. The object 110 is part of a wall of a steel pipe and comprises an exemplary flaw 120. The flaw 120 is situated in an inner region of the object 110 and is not visible from outside of the object 110. A transducer 130, which is part of the exemplary ultrasonic testing device 100, is used for sending ultrasonic pulses into the object 110, for receiving echo signals, and for converting the echo signals into electrical signals.

Typically, the transducer 130 converts electric energy into ultrasonic waves, transmits the ultrasonic waves to the object, receives ultrasonic waves from the object, and converts the received ultrasonic waves into an electric signal. Ultrasonic waves reflected from an inner region of the object to which the ultrasonic waves have been transmitted are received in order to produce an echo signal. The echo signal is converted into an electrical signal by the transducer 130. This method is known as "pulse-echo method". A method used in further typical embodiments is, for example, "through—transmission" ultrasound, where two probes are used: one as transmitter and one as receiver.

The exemplary transducer 130 of FIG. 1 is movable along a direction indicated by an arrow 140. The transducer 130 may be mounted to a rail (not shown) allowing a movement in the direction of the arrow 140.

Further typical embodiments use a robot having some degrees of freedom, e.g., 4, 5, or 6 degrees of freedom, for moving the transducer. Thereby, a free moving path for the transducer may be programmed.

By moving the transducer 130, different scan regions 150-161 of the object 110 can be scanned with the transducer 130. The scan regions 150-161 are situated in a scanning plane side by side in the object 110. The scanning plane lies along the lines of the scan regions 150-161 depicted in FIG. 1. The flaw 120 lays within the scan regions 155-159. Every one of the scan regions 150-161 is scanned with ultrasound by the transducer 130.

Typical embodiments include the transducer 130 being movable along one direction for scanning different scan regions situated side by side in a scanning plane of the scanned object. The transducer 130 can be movable to a further direction providing a scan of further regions of the object. Transducers 130 being moveable in two directions, for example, two orthographic directions, make a scanning of the whole object possible. The scan regions are situated side by side in a number of scanning planes being parallel to each other.

The transducer 130 produces electrical signals that are representative for the received ultrasonic waves. The electrical signals are transmitted to a gating unit 170. The gating unit 170 is configured for gating the electrical signals with a gating time to provide gated signals. The gating time of the gating process differs for the different scan regions 150-161, i.e., at least two of the scans or electrical signals of the respective two of the scan regions 150-161 are gated with different gating times. However, scans of some of the scan regions 150-161 can be gated with the same gating time.

Different gating times for different scan regions provide electrical signals being adapted to represent a defined sub-region of all scan regions. By doing so, the investigation is restricted to the sub-region providing clearer results in a C-mode image. Typical embodiments provide a C-mode image using the gated signals. The B-mode image is typically a B-mode live image. A fast analysis of data is possible using a B-mode live image. Further embodiments use fixed B-mode images. Fixed B-mode images use less computing time. The different gating times are typically adjustable to sub-regions of interest of the object, e.g. a sub-region with a flaw. The resulting C-mode image is easier to be read by a user. Herein, the terms "B-scan" and "B-mode image" are used as a term for B-mode images having parallel lines. "S-mode images" ("S-scan") is used for scans or images having lines being tilted. The principles disclosed in connection with B-mode images may also be used for S-mode images.

Figure 2:
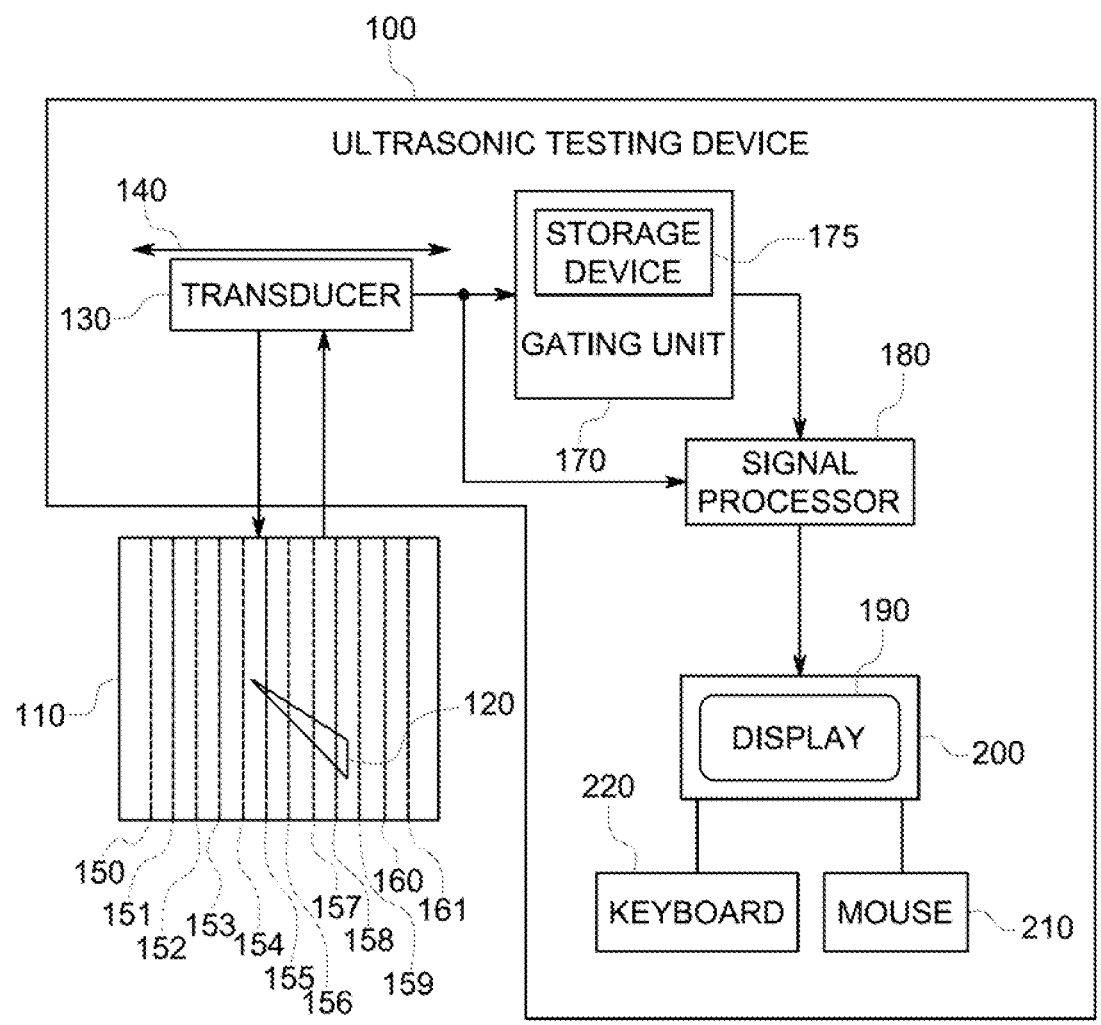
FIG. 2 is a schematic view of an ultrasonic scanning device according to embodiments.

In FIG. 2, a partly sectional schematic view of a typical ultrasonic testing device 100 used for testing an object 110 is shown. The embodiment of the ultrasonic testing device 100 of FIG. 2 corresponds to the ultrasonic testing device 100 of FIG. 1. However, the embodiment of the ultrasonic testing device 100 of FIG. 2 includes some additional features.

The gating unit 170 shown in FIG. 2 comprises a storage device 175. The storage device 175 is used to store the gating times used for the different scan regions 150-161. The gating unit 170 applies the different gating times depending on the respective scan regions 150-161. In the example shown in FIG. 2, the gating times would typically be adjusted to include the flaw 120. According to embodiments, it's the vicinity but not all of the rest of the scanned volume of the object 110 would also be included by the gating times.

According to embodiments, the gating unit and eventually the storage device are part of a computer, e.g. a personal computer, a desktop computer or an embedded system, wherein the computer is typically additionally used for further processing of the gated signals produced by the gating unit. Further typical embodiments include a stand-alone gating unit which is not necessarily part of a computer. A computer may be used as an output device, e.g. for a B-mode image or a C-mode image. A stand-alone gating unit is more flexible to use in connection with an ultrasonic scanner working in real time.

The electrical signals are transferred to a signal processor 180. The signal processor 180 is configured to generate a B-mode image using the electrical signals. In the B-mode image, the electrical signals are represented by lines that are color coded. The lines are restricted to the area given by the gating times used in the gating unit 170. In typical embodiments, a gating threshold is applied by the signal processor 180. The gating threshold can be used to trigger an evaluation of the object in a further processing step after the scanning. For instance, the evaluation can be triggered in case the amplitude of the electrical signal between the gating times gets higher than the gating threshold.

Electrical signals are produced when the object is scanned. Each scan and its respective electrical signal can be used to produce an A-mode image. A-mode images are representations over time of the ultrasonic echoes received by the probe. The amplitude of the received signal, i.e., of the electrical signal, is depicted over time.

In the embodiment shown in FIG. 2, the B-mode image produced by the signal processor 180 is displayed on a display 190. Typically, A-mode images or B-mode images are displayed as a live curve on the display 190. In embodiments, the display 190 is capable of displaying a C-mode image using the gated signals of the gating unit 170.

The gating times are used to confine the electrical signal to an area of interest. Only the part of the electrical signal between the two gating times is used for an evaluation process or for processing a C-mode image. A number of A-mode images can be used to generate a B-mode image by depicting the several A-mode images as color coded lines. Thereby, the color can represent the amplitude. By arranging several of such lines one next to the other, the B-mode image is generated. In the B-mode image, the gating times may be represented by gating lines or gating areas, wherein fixed gating times for all electrical signals of all scan regions lead to gating lines which are perpendicular to the lines of the A-mode images.

In typical embodiments, different gating times can be set for different scan regions or different electrical signals. Typically, the gating times represent the boundary of the object or a boundary between two layers of material of the object. Such boundaries produce echoes. However, echoes produced by these boundaries do not necessarily represent damages or flaws but may be used for geometry monitoring or other evaluations. In this case, these echoes are part of a gating time.

In typical embodiments described herein, the gating threshold is a fixed value. Thereby, flaws may be reliably detected. In further typical embodiments described herein, the gating threshold may be different for different scans, scanning regions, electrical signals, or A-mode images. Gating thresholds being different for different scan regions allow a more confined analysis of the object. By way of example, the gating threshold can be adjusted to different materials in different layers of the material.

As mentioned previously, a fixed gating time for all electrical signals is depicted in the B-mode image as a line being perpendicular to the several lines representing the A-mode images. When using different gating times for the several electrical signals representing scans of different areas of the object, the curve may be tilted or may even have jumps or be curved. Herein the expressions "curve" and "gating line" are used for curves or straight lines representing the gating times in the B-mode image.

The display 190 is part of a computer 200. A mouse 210 and a keyboard 220 or other kinds of Human Interface devices like trackballs are connected to the computer. An input is received from a user by using the mouse 210 and the keyboard 220. The gating time or the several gating times are adjusted depending on the input. These adjusted gating times are displayed on the display, e.g., by adjusting the curve representing the gating times.

Receiving the input from a user typically includes detecting at least one position of a cursor on the display. The position of the cursor may be altered by a user using the mouse or the keyboard. In typical embodiments described herein, the curve is calculated depending on the at least one cursor position and subsequently, the curve is drawn on the display. Thereby, the user can easily see which areas are gated by the gating times.

Furthermore, in typical embodiments described herein, the gating threshold can be input by a user. Thereby, the user may adjust the gating threshold for different regions of the object, e.g., in case the object comprises several layers including different materials. Moreover, known flaws may be gated out by adjusting the gating times or the gating threshold. Further exemplary embodiments described herein include a threshold which can vary over the scanned area. By doing so, known local areas producing a high amplitude ultrasonic echo can be ruled out.

Typically, a free form surface is calculated based on the at least one cursor position. In typical embodiments, the free form surface is drawn on the display. Thereby, the free form surface may be used to calculate the gating times or the threshold based on the coordinates of the free form surface. This allows a free definition of the threshold using the free form surface defined by the input of the user. An adequate visualization for this may also be done by a three dimensional B-scan or a three-dimensional B-mode image.

In typical embodiments, a graphic user interface is used for receiving the input of the user. A graphic user interface allows information to be input into the computer used for displaying the B-mode image with the curve representing the gating times. A free form surface can easily be input using a graphic user interface.

Figure 3:
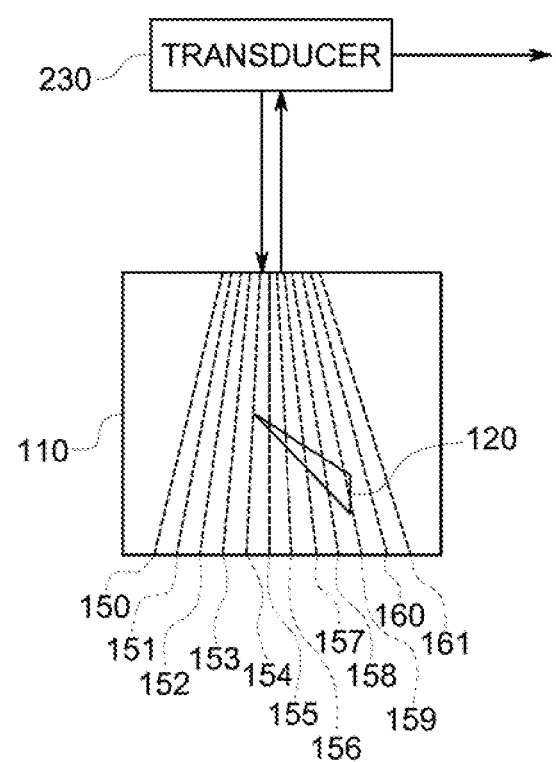
FIG. 3 shows schematically a detail of an ultrasonic scanning device according to embodiments described herein.

In FIG. 3, embodiments of a transducer 230 are shown. The transducer 230 shown in FIG. 3 uses a phased array ultrasonic probe and is intended to be used in connection with the ultrasonic devices described herein. The transducer 230 replaces the transducer 130. The phased array technique of the transducer 230 allows a scanning of a region of the object 110 by using overlapping fields. The overlapping fields are produced with different phasing for scanning different regions of the object 110. Therefore, a movement of the transducer 230 along a longitudinal moving direction is not necessary to scan a 2D-region of the object 110.

The scan regions 150-161 may be tilted when using a phased array ultrasonic probe with the transducer 230. The tilted scan regions 150-161 are shown in FIG. 3. The flaw 120 can clearly be detected. When depicting a B-mode image on a display, the tilted scan regions 150-161 are typically considered by plotting the several lines not in a parallel manner. The several lines representing color coded A-mode images are plotted with the tilting angle which has been used in scanning the object with the phased array ultrasonic probe.

Typical embodiments described herein use a phased array ultrasonic probe. Phased array ultrasonic probes scanning a 2D region, as well as phased array ultrasonic probes scanning a 3D region, may be applied. The scanning of a 2D or a 3D region with a phased array ultrasonic probe may be faster. A phased array probe may be more comfortable for the user or provide an increased level of test-information.

Figure 4:
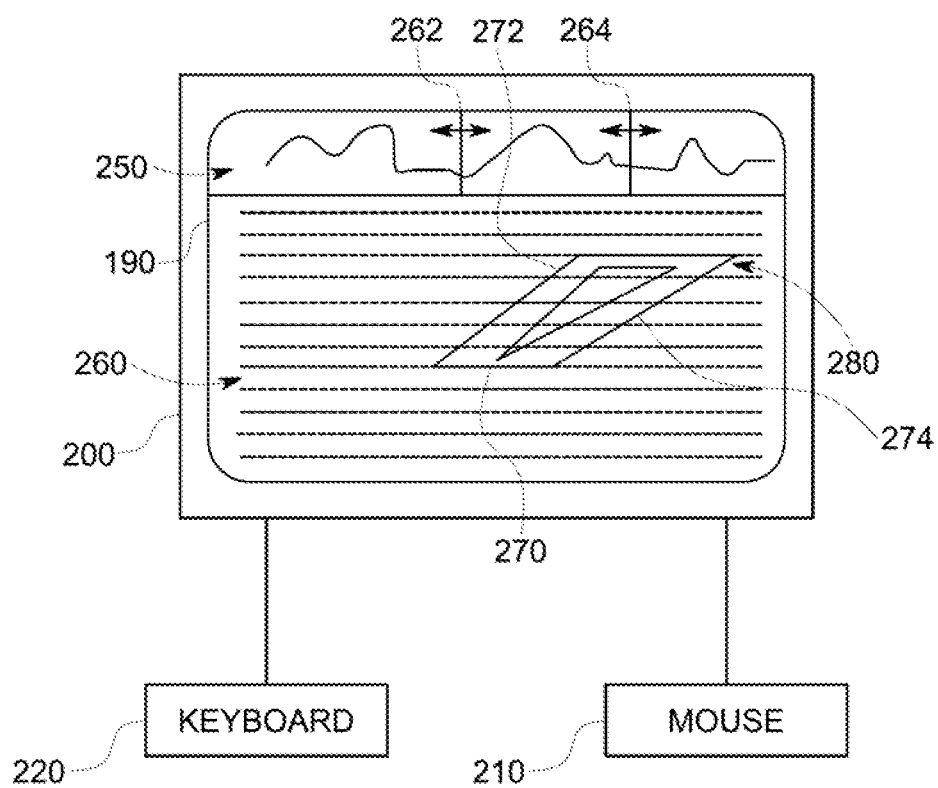
FIG. 4 shows schematically a detail of the ultrasonic scanning device according to the embodiment of FIG. 2.

The computer 200 with the display 190 of FIG. 3 is shown in FIG. 4 in more detail. In particular, an A-mode image 250 and a B-mode image 260 having parallel lines are shown on the display 190 in FIG. 4. The A-mode image 250 is in the upper part of the display 190. The shown graph is the amplitude of the ultrasonic echo depicted over time. It should be noted that the time corresponds to the depth in the object 110, since the running time of the ultrasonic signal is proportional to the depth. Two vertical lines represent the gating times, namely a gating start time 262 and a gating finish time 264. The gating times 262, 264 can be adjusted for different A-mode images or different electrical signals.

In the lower part of the display 190 shown in FIG. 4, the B-mode image 260 is displayed on the display 190. The B-mode image 260 is an addition of multiple A-mode images, one of which is the A-mode image 250 depicted in the upper part of the display 190. The B-mode image 260 is a classical B-mode image having parallel lines and has gating times which are confined to the flaw 120. It should be noted that the flaw 120 is only shown for the sake of clarity in FIG. 4. Typically, the flaw 120 cannot be seen on the display 190 but the position of the flaw 120 is identifiable by the color coding of the B-mode image 260. In the black and white depiction of FIG. 4, the flaw 120 is explicitly shown in FIG. 4.

In the B-mode image 260, a polygon 270 is shown. A left boundary 272 and a right boundary 274 of the polygon 270 represent the gating times applied to the electrical signals in the B-mode image 260. By showing the polygon 270, a user may easily identify the gated region in the scanned object 110. Furthermore, a cursor 280 is shown in FIG. 4. The cursor 280 can be moved by moving the mouse 210 as known from a personal computer. By using the cursor 280, a user may alter the position of the polygon 270. The lines or boundaries 272 and 274 of the polygon 270 correspond to the curve, based on which in typical embodiments the gating times are calculated. Hence, by altering the position or the form of the polygon 270, a user may adjust the gating times.

Typically, a polygon can be shown in the B-mode image or S-mode image representing the boundaries which are used for the calculation of the gating times. This means, that the gating of the electrical signals depends on the coordinates of the boundaries in the B-mode image or S-mode image. The boundaries represent the above mentioned "curves".

Figure 5:
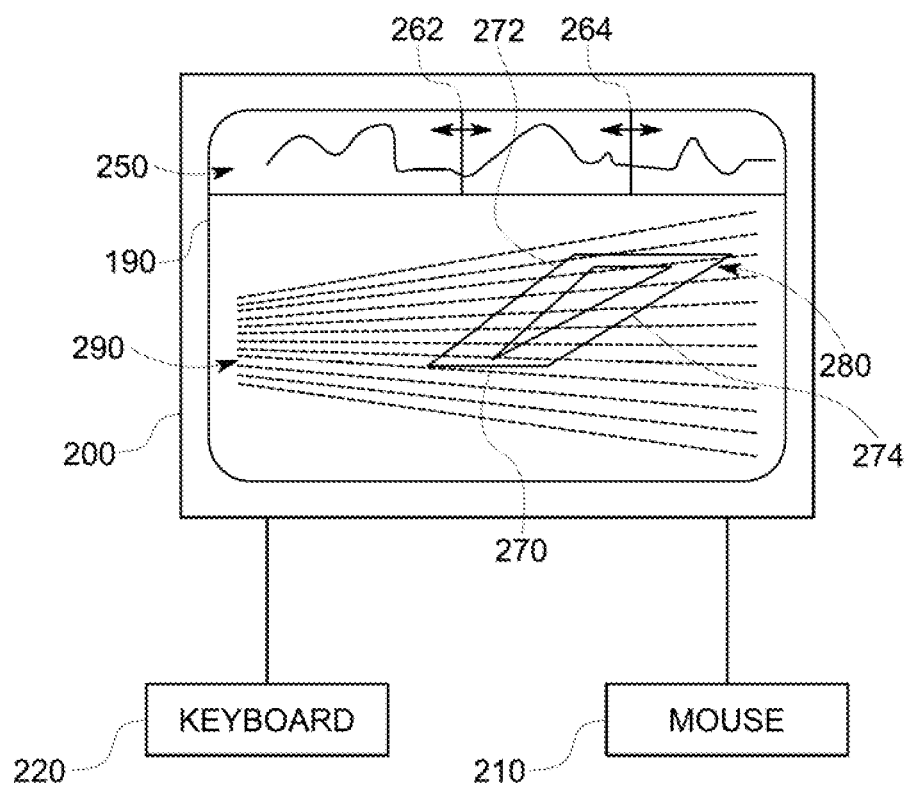
FIG. 5 shows schematically a detail of the embodiment of FIG. 2 in case the phased array probe of FIG. 3 is used.

FIG. 5 shows the same setup as FIG. 4, wherein the display 190 is used to display an S-mode image 290 as a special, "scan—geometry correlated", form of a B-mode image. The S-mode image is based on a scan using the phased array probe 230 of FIG. 3. The difference to the B-mode 260 image shown in FIG. 4 is a presentation of the A-scans in the correct angle.

The signal processing must be able to identify the angles used by the phased array probe during scanning of the object 110. All other features shown in FIG. 4 apply to the setup shown in FIG. 4 as well, especially the polygon 270 being used for identifying gated region of the object 110. During processing, the gating times are calculated based on the lines or boundaries of the polygon 270.

Figure 6:
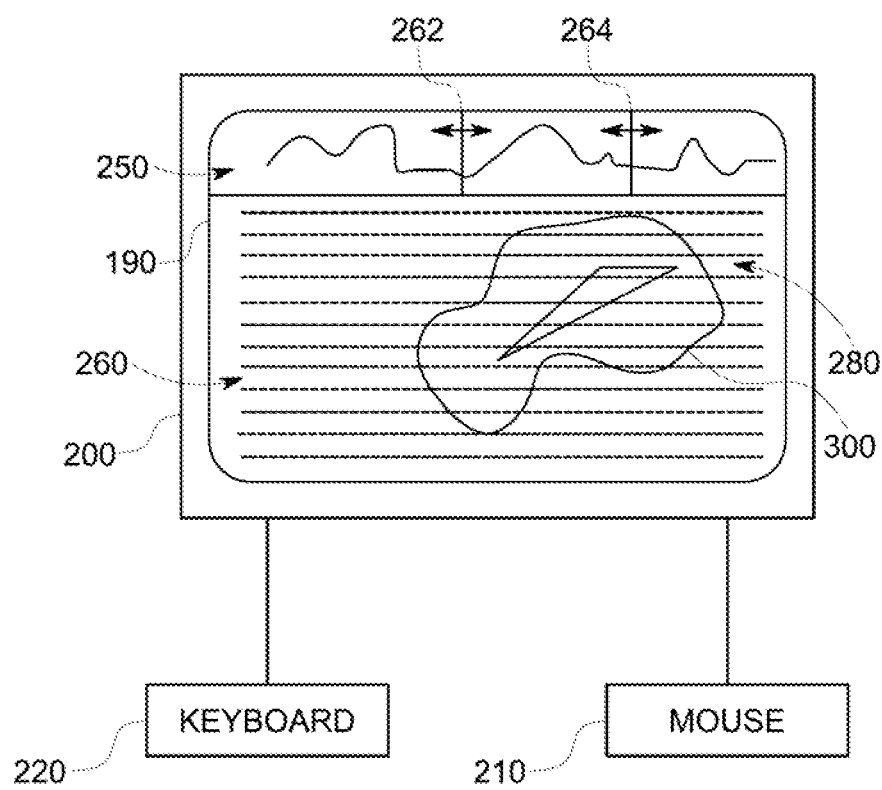
FIG. 6 shows schematically the application of a free form surface in the ultrasonic scanning device of the embodiment of FIG. 2.

In FIG. 6, the application of a free form surface 300 in connection with a detail of FIG. 2 is shown. As explained above, a free form surface may be used to set gating times and thresholds depending on the region of interest of the object 110. The free form surface 300 may be drawn by a use of the cursor 280 using the mouse 210. By doing so the adjustment of a varying threshold over a region of interest is facilitated.

Figure 7:
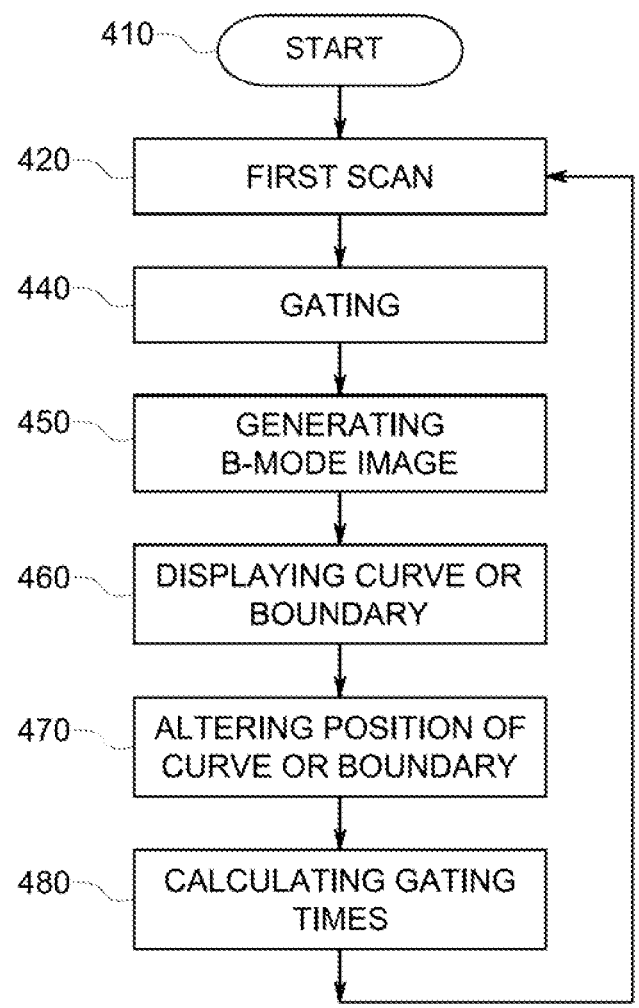
FIG. 7 shows a method according to embodiments in a schematic flow chart.

In FIG. 7, a method of a typical embodiment described herein is shown in a schematic diagram. After the method starts (410), a first scan of multiple scan regions of the object is carried out (420).

The method gates the different electrical signals of the different scans with gating times (440) for the testing process. Thereby, different gating times are used for every electrical signal. The results are gated signals. It should be noted that every electrical signal can be depicted as an A-mode image. The respective A-mode images are representations of the respective scan regions. The gating times depend on the respective scan region. Hence, different gating times are used for the different scan regions.

Typically, for each single scan region gating times are defined, e.g., a gate start time and a gate finish time. Typical embodiments use identical gating times for more than one scan region. However, at least one of all of the scan regions has different gating times. Thereby, the computing time for calculating the gating times may be reduced.

A B-mode image is generated by a signal processor (450). Subsequently, the B-mode image is displayed on a display for a user. Furthermore, at least one curve is shown on the display (460). Typically, more than one curve is shown, e.g., a polygon. The curve or boundary represents the gating times in the B-mode image. Thereby, the gating times are displayed for a user together with the B-mode image making recognition of data easy for a user.

The user may alter the position of the curve or the boundary by using, a cursor (470). Thereby, the gating times may be adjusted by the User. Gating times are calculated based on the altered positions of the curve (480). The method jumps back to again to receive data of a new scan and gate the electrical signals of the ultrasonic scan with the newly calculated gating times based on the altered positions of the curve. The method may be stopped by the user in case the user does not alter the position of the curve, i.e. the Rating times.

In typical embodiments described herein, the method starts with producing a B-mode image. The B-mode image is shown on the display with preliminary boundaries for gating times to enable the user to set the curves representing the boundaries for an area of interest. These boundaries or curves are used to calculate gating times. With these gating times, a C-mode image may be produced or other processing may be carried out. Typical embodiments allow a further alteration of the at least one boundary in the B-mode image. Typically, on every alteration of the boundary, the gating times are recalculated. The B-mode image is typically a live image, wherein the scanning of the object is repeated.

Typical embodiments present a classical B-mode image having parallel lines to the user. All features named with the presentation or processing of a B-mode image may be applied to S-mode images as well. Generally, an S-mode image is a special form of a B-mode image, wherein the only difference is a presentation of the data with the angles used during scanning, e.g., by a phased array probe.

This written description uses examples to disclose the invention, including the best mode, and also to enable any person skilled in the art to practice the invention, including making and using any devices or systems and performing any incorporated methods. While various specific embodiments have been disclosed in the foregoing, those skilled in the art will recognize that the spirit and scope of the claims allows for equally effective modifications. Especially, mutually non-exclusive features of the embodiments described above may be combined with each other. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for ultrasonic testing of an object, the method comprising:
   a) ultrasonic scanning of a plurality of scan regions of the object, thereby generating ultrasonic echoes;
   b) converting the ultrasonic echoes of the ultrasonic scanning into a plurality of electrical signals;
   c) gating the electrical signals to provide gated signals; wherein different gating times are used for the electrical signals, the gating times each comprising a gating start time and a gating finish time;
   d) processing the electrical signals to obtain an ultrasonic B-mode image;
   e) receiving an input from a user by detecting the user adjusting at least one boundary position on the display using a cursor, the at least one boundary position defining at least one of the gating start time and the gating finish time; and
   f) adjusting at least one of the gating start time and the gating finish time in response to the user adjusting the at least one boundary position on the display.

2. The method according to claim 1, wherein the gating times depend on the respective scan region.

3. The method according to claim 1, comprising
   displaying the adjusted gating times with the B-mode image on a display.

4. The method according to claim 1, comprising calculating a curve depending on the input from the user and drawing the curve on the display.

5. The method according to claim 4, wherein the different gating times are calculated based on coordinates of the curve.

6. The method according to claim 1, comprising calculating a free form surface depending on the input from the user and drawing the free form snake on the display.

7. The method according to claim 6, wherein the gating times is calculated based on coordinates of the free form surface.

8. The method according to claim 7, wherein the gating comprises employing a gating threshold, the gating threshold being calculated based on coordinates of the free form surface.

9. The method according to claim 1, wherein a graphic user interface is used for receiving the input from the user.

10. Ultrasonic testing device for testing an object, comprising:
    a) an ultrasonic transducer for scanning a plurality of scan regions of the object and for convening ultrasonic echoes into electrical signals;

b) a gating unit configured for gating the electrical signals with a gating time to provide gated signals, the gating time comprising a gating start time and a gating finish time, wherein the gating time depends on the respective scan region;
c) a signal processor configured to generate a B-Mode image;
d) a display configured to display the B-mode image and to display the gating time as a curve, the curve having a first portion indicating the gating start time and a second portion indicating the gating finish time;
e) an input unit for receiving an input from a user, the input unit being configured for enabling the user to adjust a position of the curve on the display and for detecting the adjusted position of the curve on the display as the input, the adjusted position of the curve indicating an adjusted gating start time, an adjusted gating finish time, or both; and wherein the gating unit is configured to adjust the gating time in response to detecting the adjusted position of the curve on the display.

11. Ultrasonic testing device according to claim 10, the display and the input unit being configured with a graphic user interface.

12. Ultrasonic testing device according to claim 10, the ultrasonic transducer comprising a phased array.

13. A method for testing an object with an ultrasonic testing device comprising a display, the method comprising:
a) scanning a plurality of scan regions of the object to obtain to plurality of electrical signals according to a eating time for each of the electrical signals;
b) processing the electrical signals to obtain a B-mode image and displaying the B-mode image on the display;
c) receiving an input from a user manipulating a cursor on the display to position a boundary in the B-mode image, the boundary defining at least one of a gating start time and a gating finish time of the gating time for each of the electrical signals; and
d) processing of the electrical signals, wherein the processing comprises a gating of the electrical signals according to the gating times defined by display coordinates the boundary in the B-mode image.

14. The method according to claim 13, comprising receiving the input from the user by a graphic user interface.

15. The method according to claim 13, comprising calculating the gating times for the gating of the electrical signals according to the coordinates of the boundary.

16. The method of claim 1, wherein the step e) comprises detecting the user adjusting at least two cursor positions of the cursor on the display, a first one of the at least two cursor positions corresponding to the gating start time and a second one of the at least two cursor positions corresponding to the gating finish time, and wherein the step f) comprises adjusting both the gating start time and the gating finish time in response to the user adjusting the first and second cursor positions.

17. The method of claim 16, further comprising displaying the B-mode image on the display, and displaying the first and second cursor positions in relation to the B-mode image.

* * * * *

UNITED STATES PATENT AND TRADEMARK OFFICE
CERTIFICATE OF CORRECTION

PATENT NO. : 8,770,029 B2
APPLICATION NO. : 13/252435
DATED : July 8, 2014
INVENTOR(S) : Falter et al.

It is certified that error appears in the above-identified patent and that said Letters Patent is hereby corrected as shown below:

In the Specification

In Column 7, Line 13, delete "so the" and insert -- so, the --, therefor.

In Column 7, Line 43, delete "using," and insert -- using --, therefor.

In Column 7, Line 44, delete "User." and insert -- user. --, therefor.

In Column 7, Line 50, delete "Rating" and insert -- gating --, therefor.

In the Claims

In Column 8, Line 43, in Claim 3, delete "comprising" and insert -- comprising: --, therefor.

In Column 8, Line 53, in Claim 6, delete "snake" and insert -- surface --, therefor.

In Column 8, Line 63, in Claim 10, delete "Ultrasonic" and insert -- An ultrasonic --, therefor.

In Column 8, Line 66, in Claim 10, delete "convening" and insert -- converting --, therefor.

In Column 9, Line 6, in Claim 10, delete "B-Mode" and insert -- B-mode --, therefor.

In Column 9, Line 21, in Claim 11, delete "Ultrasonic" and insert -- The ultrasonic --, therefor.

In Column 9, Line 24, in Claim 12, delete "Ultrasonic" and insert -- The ultrasonic --, therefor.

In Column 9, Line 29, in Claim 13, delete "obtain to" and insert -- obtain a --, therefor.

Signed and Sealed this
Thirty-first Day of March, 2015

Michelle K. Lee
*Director of the United States Patent and Trademark Office*

In Column 9, Line 30, in Claim 13, delete "eating" and insert -- gating --, therefor.

In Column 10, Line 10, in Claim 13, delete "coordinates the" and insert -- coordinates of the --, therefor.